United States Patent
Bernard et al.

(10) Patent No.: US 11,308,594 B2
(45) Date of Patent: Apr. 19, 2022

(54) TOMOSYNTHESIS DATASET GENERATION USING PRE-EXPOSURE ACQUISITION

(71) Applicant: GE Precision Healthcare LLC, Milwaukee, WI (US)

(72) Inventors: Sylvain Bernard, Buc (FR); Remy Klausz, Buc (FR); Veronique Felix, Gif-sur-Yvette (FR); Xavier Mancardi, Buc (FR)

(73) Assignee: GE Precision Healthcare LLC, Milwaukee, WI (US)

( * ) Notice: Subject to any disclaimer, the term of this patent is extended or adjusted under 35 U.S.C. 154(b) by 225 days.

(21) Appl. No.: 16/875,819

(22) Filed: May 15, 2020

(65) Prior Publication Data

US 2021/0358094 A1 Nov. 18, 2021

(51) Int. Cl.
| | |
|---|---|
| *A61B 6/00* | (2006.01) |
| *G06T 5/50* | (2006.01) |
| *G06T 7/30* | (2017.01) |
| *A61B 6/02* | (2006.01) |
| *A61B 6/04* | (2006.01) |
| *G06T 11/00* | (2006.01) |

(52) U.S. Cl.
CPC .............. *G06T 5/50* (2013.01); *A61B 6/025* (2013.01); *A61B 6/0414* (2013.01); *A61B 6/4021* (2013.01); *A61B 6/4291* (2013.01); *A61B 6/488* (2013.01); *A61B 6/502* (2013.01); *A61B 6/5211* (2013.01); *A61B 6/5223* (2013.01); *G06T 7/30* (2017.01); *G06T 11/005* (2013.01); *G06T 11/008* (2013.01); *G06T 2207/10072* (2013.01); *G06T 2207/10116* (2013.01); *G06T 2207/20221* (2013.01); *G06T 2207/30068* (2013.01)

(58) Field of Classification Search
CPC ...... A61B 6/025; A61B 6/5211; A61B 6/5223
See application file for complete search history.

(56) References Cited

U.S. PATENT DOCUMENTS

| | | |
|---|---|---|
| 6,292,536 B1 | 9/2001 | Chichereau et al. |
| 6,556,655 B1 | 4/2003 | Chichereau et al. |
| 9,842,415 B2 | 12/2017 | Bernard et al. |
| 10,092,262 B2 | 10/2018 | Bernard |
| 10,096,106 B2 | 10/2018 | Bernard |
| 2012/0063567 A1* | 3/2012 | Smith .................. A61B 8/0825 378/37 |

OTHER PUBLICATIONS

EP application 21170809.4 filed Apr. 27, 2021—Extended Search Report dated Oct. 8, 2021, 7 pages.

* cited by examiner

Primary Examiner — Dani Fox
(74) Attorney, Agent, or Firm — McCoy Russell LLP (57) ABSTRACT

Systems and methods for synthesizing a two-dimensional (2D) image of an organ of a patient by obtaining an pre-exposure x-ray image of the organ in order to ascertain parameters needed for acquisition of 2D (tomosynthesis) projection images of the organ, imaging the organ to obtain a plurality of 2D (tomosynthesis) projection images of the organ, and generating a synthetic 2D image of the organ from a combination of both the plurality of tomosynthesis projection images and the pre-exposure x-ray image.

22 Claims, 5 Drawing Sheets

TOMOSYNTHESIS DATASET GENERATION USING PRE-EXPOSURE ACQUISITION

FIELD

Embodiments of the subject matter disclosed herein relate the field of tomosynthesis and tomosynthesis dataset generation using pre-exposure acquisition, and, more particularly, synthesizing a 2D radiographic image using tomosynthesis projection images and a pre-exposure x-ray image.

BACKGROUND

Various radiographic imaging techniques have become valuable in the medical industry for non-invasively examining an object of interest in the human body, and improvements in image content, image type availability, and image quality continue to be desirable. For example, mammography is a common and standard screening practice for detecting and diagnosing breast cancer. Standard two-dimensional (2D) mammograms involve positioning the breast between a source (emitter) of x-rays and a detector, exposing the detector to x-rays emitting from the source and passing through the breast tissue, and generating a 2D image from the data received by the detector. The resulting standard (or full field) 2D mammogram images, however, may be limited by tissue superimposition, which is where abnormalities within the imaged tissue may be masked by tissue above and/or below the abnormalities.

Digital breast tomosynthesis (DBT) is a radiographic imaging technique that provides a three-dimensional (3D) (volume) representation of the breast tissue, viewable as a series of slices or layers. The slices are reconstructed from projections of the object of interest taken at various angles, obtained, for example, by moving the x-ray emitter (source of x-rays) throughout an arc over the target object and detector therebeneath. The 3D slices generated using tomosysthesis (or, simply, DBT) provide the medical practitioner with a capability to better examine the imaged object, by viewing multiple layers (slices) of the reconstructed 3D volume to, for example, locate areas of particular interest within the imaged object. However, the DBT images are generally not directly comparable to the 2D images generated using conventional mammography methods due, at least in part, to the geometric lay out.

As mentioned, the 2D image is the projection of the full volume whereas DBT generates a set of slices throughout the volume. With DBT, the radiologist has to observe a significant number of images (all layers) whereas with a 2D image only one image is observed. This significantly increases the reading time (by a factor 2 or more). Another limitation is when a patient presents the medical professional with a prior simple 2D image it is difficult to compare it with the set of slices procured by DBT; and a 2D image must be acquired again for comparison, resulting in additional irradiation of the patient. For these and other reasons, even as improvements are made in DBT techniques and as DBT technology becomes more commonly adopted and used by medical practitioners, the provision of the more well-known 2D mammography images is still desired by medical professionals and radiologists.

To address the desire for 2D mammograms in addition to the provision of the relatively more recently available tomosynthesis images, a combination acquisition of images may be performed. That is, both 2D mammogram and 3D digital breast tomosynthesis images are acquired for the same object of interest. However, since the average dose from tomosynthesis imaging is higher than or approximately the same as the conventional mammogram 2D imaging, the radiation exposure required for a combination 2D mammogram plus DBT may be roughly double that of one or the other method alone. There is a need, therefore, to generate or acquire the information of known 2D mammograms in addition to DBT images without, effectively, performing two examinations, in order to reduce and minimize the total x-ray dose.

Methods for synthesizing 2D mammogram images using tomosynthesis and methods for tomosynthesis dataset generation to obtain synthesized 2D images of improved quality while minimizing x-ray dosage received by the target object are therefore desirable.

BRIEF DESCRIPTION

In one aspect, the present disclosure is directed to a method for obtaining at least one enhanced image of an object of interest using a system comprising an x-ray source facing a detector. In an exemplary embodiment, a method of generating a synthesized 2D image of an organ of a patient includes obtaining a pre-exposure image of the organ by exposing the organ with x-ray energization; obtaining, based upon the pre-exposure image acquired, a plurality of two-dimensional (2D) (or tomosynthesis) projection images of the organ by rotating the x-ray emitter to a plurality of orientations relative to the organ and emitting x-ray energization from the emitter for each projection image of the plurality of projection images; and generating a synthetic 2D image of the organ from the pre-exposure image and the plurality of tomosynthesis projection images.

In one aspect, the method further includes merging the pre-exposure image with at least one of the tomosynthesis projection images closest to a source position to create a merged pre-exposure image, the source position being the position at which the pre-exposure image is obtained.

In one aspect, the merging is performed using a registration algorithm in case of patient motion and/or to compensate for differences in the acquisition angles of the pre-exposure image and the at least one of the tomosynthesis projections.

In one aspect, the method further includes utilizing the pre-exposure image acquired as a baseline image; and generating a synthetic 2D image of the organ by enhancing the baseline image with information in the tomosynthesis projection images.

In one aspect, the method further includes utilizing one of the tomosynthesis projection image as a baseline image; and generating a synthetic 2D image of the organ by enhancing the baseline image with information in the tomosynthesis projection images and the pre-exposure image.

In one aspect, the method further includes displaying the synthetic 2D image on a display.

In one aspect, the pre-exposure image of the organ and the plurality of 2D (tomosynthesis) projection images of the organ are obtained during a same compression of the organ.

In one aspect, levels of x-ray energization used for obtaining each of the plurality of two-dimensional (2D) (tomosynthesis) projection images are lower than a level of x-ray energization used for obtaining the pre-exposure image.

In an exemplary embodiment, a method of generating a synthesized 2D image of an organ of a patient includes obtaining a pre-exposure image of the organ by exposing the organ with x-ray energization; obtaining, based on the pre-exposure image acquired, a plurality of two-dimensional (2D) (or tomosynthesis) projection images of the organ by rotating the x-ray emitter to a plurality of orientations relative to the organ and emitting x-ray energization from the emitter for each projection image of the plurality of projection images; reconstructing a 3D volume using the tomosynthesis projection images and the pre-exposure image; and generating a synthesized 2D image from the reconstructed 3D volume.

In one aspect, the pre-exposure image is included with the plurality of 2D (tomosynthesis) projection images prior to reconstructing the 3D volume and generating the synthesized 2D image.

In one aspect, one of the plurality of 2D (tomosynthesis) projection images is replaced by the pre-exposure image prior to reconstructing the 3D volume and generating the synthesized 2D image.

In one aspect, one of the plurality of 2D projection images is combined with the pre-exposure image prior to reconstructing the 3D volume and generating the synthetic 2D image.

In one aspect, the synthetic 2D image is obtained by enhancing the pre-exposure image using at least a subset of the reconstructed slices.

In one exemplary embodiment, a system for synthesizing a 2D radiographic image includes an x-ray emitter capable of producing x-rays, the x-ray emitter being rotatable to a plurality of orientations; an x-ray detector in at least partial alignment with the x-ray emitter; a processor operably connected to the x-ray emitter and the x-ray detector, the processor operates the x-ray emitter and detector to acquire a pre-exposure image of the organ and subsequently, based on the pre-exposure image acquired, operates the x-ray emitter and detector to rotate about an organ to be imaged in order to obtain a plurality of two-dimensional (2D) (or tomosynthesis) projection images of the organ, wherein the processor synthesizes a 2D image from the pre-exposure image and the plurality of tomosynthesis projection images; and a display for displaying the synthesized 2D image.

In one aspect, the processor merges the pre-exposure image with at least one of the tomosynthesis projection images to create a merged pre-exposure image; and generates the synthesized 2D image of the organ by enhancing the merged pre-exposure image with information in the tomosynthesis projection images.

In one aspect, the merging is performed using a registration algorithm in case of patient motion and/or to compensate for differences in the acquisition angles of the pre-exposure image and the at least one of the tomosynthesis projections.

In one aspect, the processor utilizes the pre-exposure image acquired as a baseline image; and generates a synthesized 2D image of the organ by enhancing the baseline image with information in the tomosynthesis projection images.

In one aspect, the processor enhances a projection image acquired during tomosynthesis exposure using data from the plurality of 2D (tomosynthesis) projection images; and generates a synthesized 2D image of the organ by using the enhanced projection image.

In one aspect, levels of x-ray energization used for obtaining each of the plurality of two-dimensional (2D) (tomosynthesis) projection images are lower than a level of x-ray energization used for obtaining the pre-exposure image.

In one aspect, the processor reconstructs a 3D volume using the 2D (tomosynthesis) projection images and the pre-exposure image; and generates a synthesized 2D image from the reconstructed 3D volume.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

The following description relates to various embodiments of systems and methods for synthesizing 2D x-ray images using digital breast tomosynthesis (DBT), to provide a synthesized 2D image using the projection image acquired from the first distinct exposure (or pre-exposure) in combination with the projection images acquired during the continuous sweep (or multiple images comprising the DBT sequence). The methods utilize the pre-exposure image used to establish parameters for acquiring the multiple DBT images, to provide an improved and enhanced synthesized 2D radiographic image.

Although the present application is presented and described in the context of mammography it is to be understood that other radiographic applications and imaging of other organs and organ systems may be performed using the systems and methods as disclosed herein.

Figure 1:
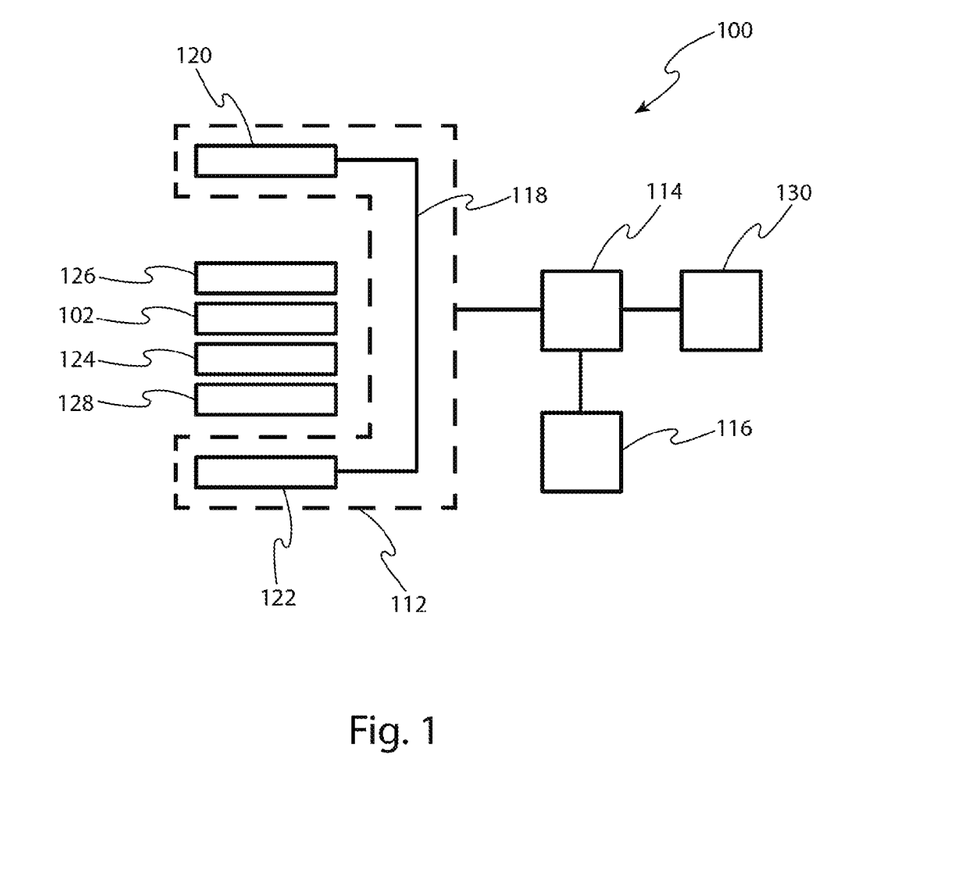
FIG. 1 is a schematic diagram of an exemplary medical imaging system for acquisition of digital breast tomosynthesis images and tomosynthesis dataset generation using pre-exposure acquisition information.
Figure 2:
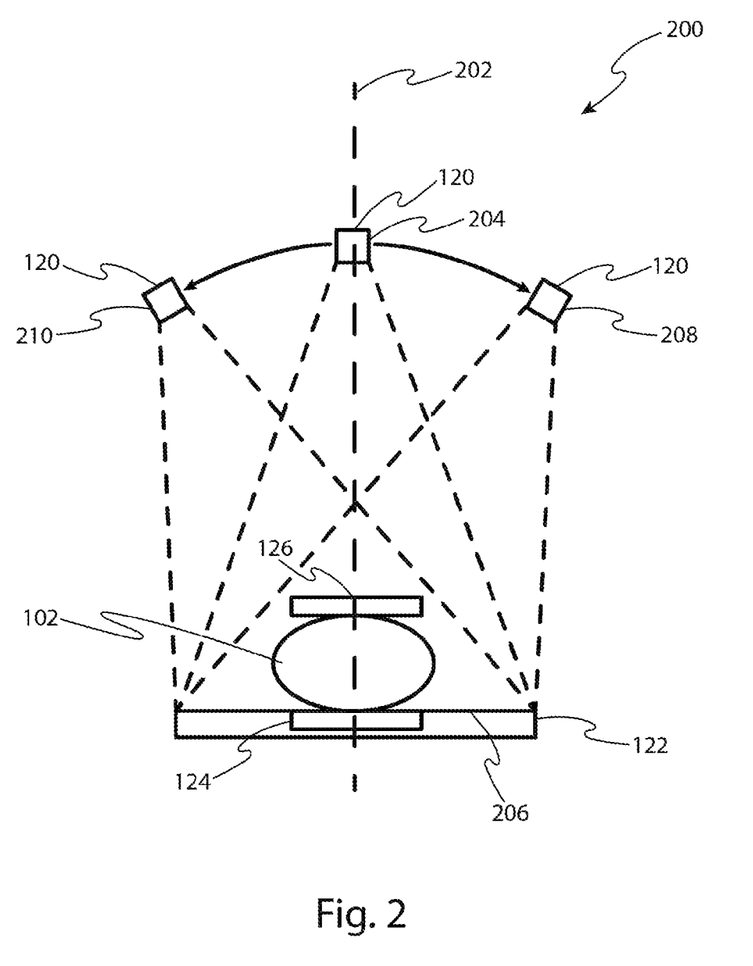
FIG. 2 depicts alignment for pre-exposure imaging and rotation of the imaging apparatus about an object to acquire DBT radiographic images, according to some embodiments.
Figure 3:
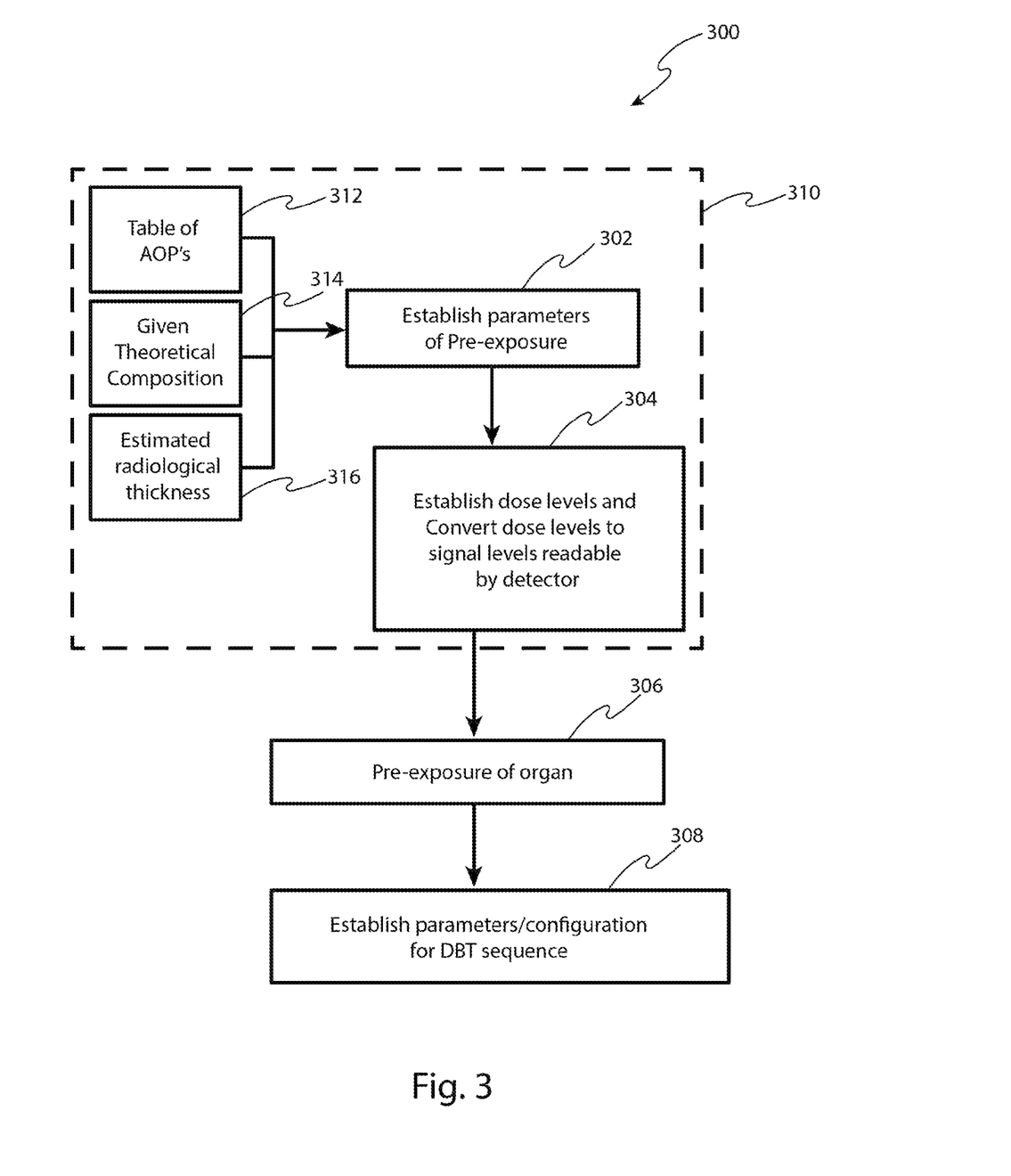
FIG. 3 is a flow chart of exemplary embodiments of methods involving pre-exposure image acquisition and determination of parameters of exposure for acquiring DBT images of a target object.
Figure 4:
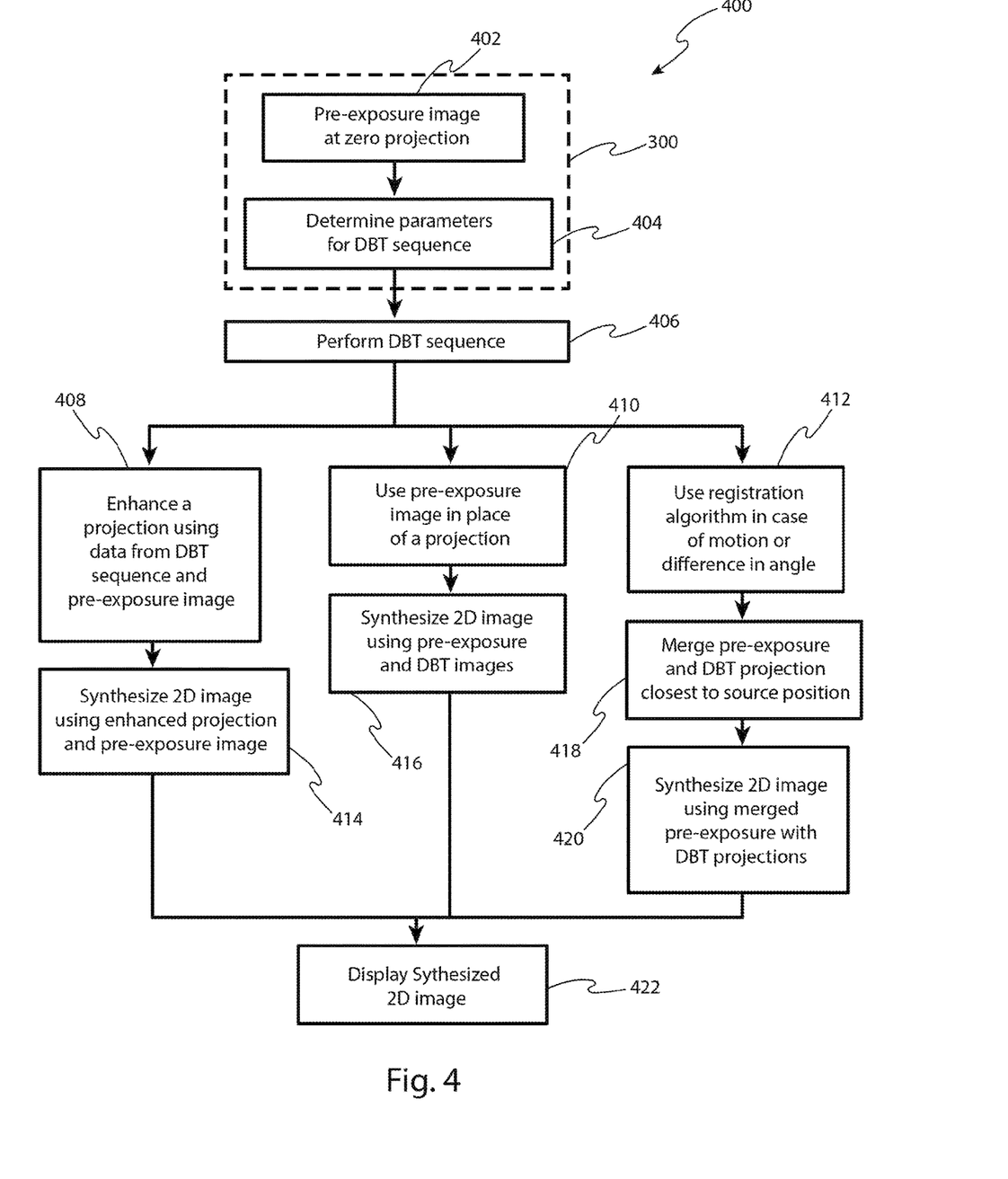
FIG. 4 is a flow chart that depicts exemplary embodiments of methods of imaging an organ of a patient using tomosynthesis and synthesizing a 2D image of the imaged organ using pre-exposure image information.
Figure 5:
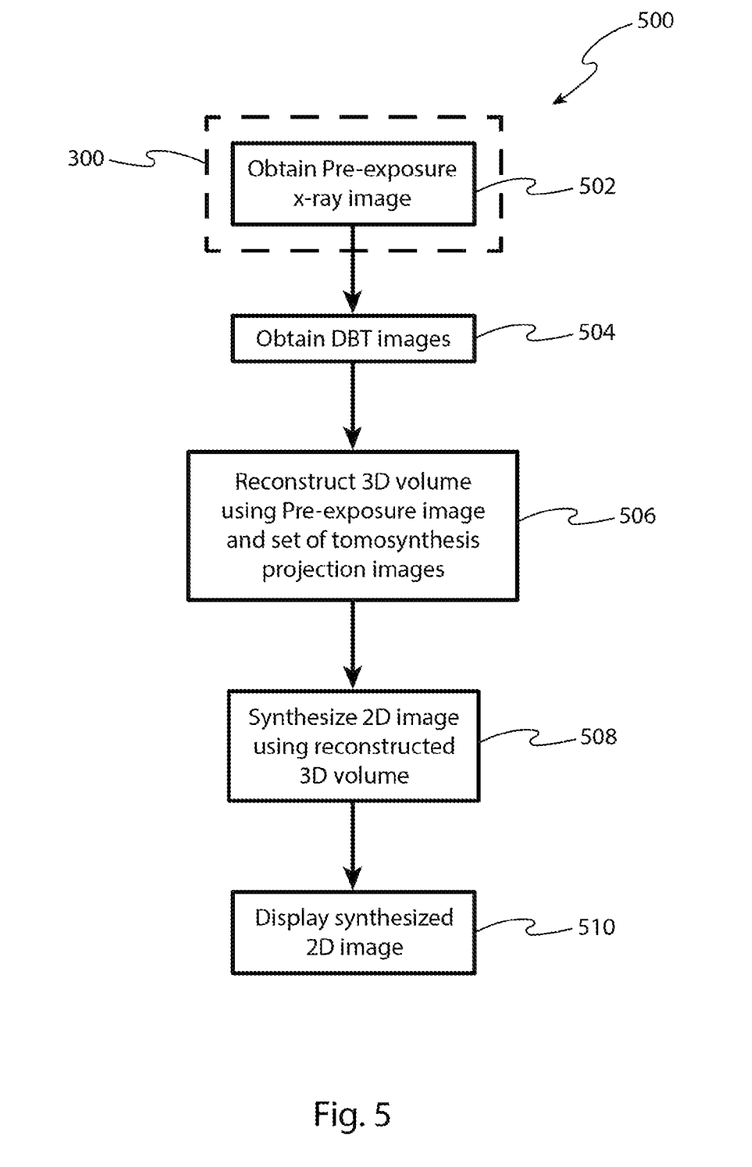
FIG. 5 is a flow chart of exemplary embodiments of methods of imaging an organ using tomosynthesis and reconstructing a 3D volume using the set of tomosynthesis projections as well as the pre-exposure image used for determination of parameters for acquiring the tomosynthesis projections.

As an overview, FIG. 1 shows an exemplary system for synthesizing a 2D radiographic image according to embodiments. FIG. 2 illustrates a portion of the system shown in FIG. 1, wherein a pre-exposure image is acquired prior to beginning the digital breast tomosynthesis (DBT) series of images, and the DBT continuous sweep or series of images at different projection angles. FIG. 3 provides a flow chart for exemplary methods involving pre-exposure image acquisition and determination of parameters of exposure for the (subsequent) DBT projections. FIGS. 4 and 5 provide flow charts for exemplary methods of synthesizing a 2D image of the target object imaged using the information from the DBT projections and the pre-exposure image acquired for determining the parameters of the subsequent DBT sequence.

Illustrated in FIG. 1 is a schematic diagram of an exemplary embodiment of a medical imaging system 100 for acquisition of digital breast tomosynthesis images and tomosynthesis dataset generation using pre-exposure acquisition information. The exemplary system 100 includes an image acquisition unit 112, an image processing unit 114, optionally a memory storage unit 130, a graphical display 116, and/or (not shown) a connection to a network for external storage and display (e.g. a picture archiving and communication system or PACS). The image acquisition unit 112 includes a c-arm 118. The c-arm 118 includes, at opposing ends, an x-ray emitter 120 and an x-ray detector 122.

The system 100 includes a lower support 124 and compression plate 126 (sometimes referred to as compression paddle 126). The organ to be imaged, for example, a breast of a patient, is placed on the lower support 124. The lower support 124 holds the organ in a relative axial alignment with the c-arm 118 between the x-ray emitter 120 and the x-ray detector 122. A compression support 126 is lowered to compress the organ 102 between the lower support 124 and the compression plate 126.

Generally speaking, compression of the organ, such as between supports 126 and 124, has been important, especially for 2D only mammography, for improved imaging quality. Compression generally helps to spread out the normal fibro glandular (or more dense) tissue of the breast making it easier for the medical practitioner/radiologist to differentiate the breast tissue and detect abnormalities that might otherwise be hidden by the overlying (or superimposed) tissue. If the breast is not well compressed, overlapping tissue may appear and be interpreted as a mass or abnormality. DBT, as mentioned, provides improvements to the issue of superimposition. Consequently, in the context of DBT, compression of the organ is mainly used for reducing the breast thickness, therefore reducing the irradiation needed for imaging, and for immobilizing the organ during the DBT acquisition sequence.

In acquiring radiographic images of the organ, the x-ray emitter 120 is operated to produce x-rays which are projected in the direction of the organ (or target object) 102. The x-rays pass through the organ 102 to the detector 122. In an exemplary embodiment, the imaging system 100 may also be provided with an anti-scatter grid 128. The anti-scatter grid 128 may include a plurality of opaque components arranged parallel to one another, in a direction parallel to the motion of the c-arm 118. Such anti-scatter grids are typically used to limit the impact of the spread of emitted x-rays within the patient's body.

The c-arm 118 may be coaxially aligned with the organ 102, for example in the compressed position exemplarily held between the lower support 124 and the compression support 126, with the c-arm 118 operable to rotate about the organ 102 held in this position. During rotation of the c-arm 118, the scatter grid 128 and detector 122 may rotate with the c-arm 118 or not. In some embodiments, the image detector 122 remains fixed during the DBT sweep. That is, in some embodiments, the organ 102 and detector 122 remain in a fixed alignment with one another while the emitter 120 moves in relation to the organ 102 (and detector 122) during the DBT sweep/sequence. In some embodiments, the whole assembly (image acquisition unit) 112 is able to rotate simultaneously to change the projection relative to patient anatomy (e.g. vertical, lateral, etc.).

Although the system 100 depicted in FIG. 1 shows the x-ray detector 122 being rotatable in conjunction with the emitter 120, such that the emitter 120 and the detector 122 are maintained in alignment, it will be recognized that in additional embodiments of medical imaging systems, the detector 122 may be held in a fixed position relative to the organ 102, for example, by locating the x-ray detector 122 in the lower support 124 (as shown in FIG. 2).

Also shown in FIG. 1, the image processing unit 114 may be connected to or incorporate a memory unit 130 which may comprise a non-transitory computer readable medium. The memory unit 130 may be located inside or outside the processor 114. The processor 114 may operate to read and/or write information from/to the memory unit 130. The memory unit 130 may comprise a hard disk or SSD or any other rewritable and/or removal storage medium, such as, for example USB flash drives, memory cards, etc. The memory unit 130 may be a ROM/RAM memory of the processor 114, flash memory, and/or memory on a remotely located server. The memory may further be programmed with computer readable instructions/code embodying one or more programs, routines, algorithms, or subroutines which is accessible by the processor 114 and executable by the processor 114 to carry out the acquisition unit control, image processing, and display functions and operations and methods as disclosed herein. In some embodiments, the image processing unit 114 may comprise, as previously mentioned, a connection to a network for external storage and display (e.g. a picture archiving and communication system or PACS), with the image processing unit 114 adapted to permit storing, retrieving, presenting, and/or sharing images produced by the system 100.

FIG. 2 illustrates exemplary relative positioning 200 of the x-ray emitter 120 during pre-exposure acquisition and DBT image acquisition. In particular, FIG. 2 depicts exemplary alignment for acquiring a pre-exposure image and exemplary movement of the x-ray emitter 120 relative to the organ (target object) 102 for performing a DBT sequence for acquiring DBT radiographic images subsequent to the pre-exposure image acquisition. As shown, the emitter 120 may be alignable to a zero ("0°") or center (or "central") position 204 along an axis 202 that is perpendicular (orthogonal) (or substantially perpendicular, to within a predetermined tolerance around 0°, e.g. a predetermined tolerance of +/−0.5°) to the detector 122. The axis 202 may be, as shown, substantially orthogonal to one or both of the organ (target object) 102 and the detector 122. In one embodiment, the orthogonal or center position 204 represents the position, within a predetermined tolerance, at which a pre-exposure image is acquired, also referred to as the source position at which the pre-exposure image is acquired, in order to establish the parameters needed for the subsequent DBT sequence of exposures (or DBT sweep). Determining the parameters needed for the subsequent DBT sequence may include, for the particular target object 102 examined, determination of an equivalent radiologic thickness, estimation of a composition of width examined, and establishing a configuration of exposure and an exposure mA·s (i.e. product of anodic current and duration of exposure).

The pre-exposure image may be similar to a standard full field digital mammography (FFDM) (or conventional 2D mammography) image except for the quantity of x-rays which, for the pre-exposure image, is maintained small enough not to significantly increase the patient irradiation. In the current state-of-the-art, the x-ray dose for a pre-exposure may be comparable to the x-ray dose used for one of the DBT projection images obtained in a (subsequently obtained) DBT sequence. Further, the pre-exposure image may be similar to a standard FFDM insofar as the pre-exposure image may be acquired in the aforementioned orthogonal or center position 204 as would a standard FFDM image, with the emitter 120 substantially lined up along the axis 202 (or zero or central projection axis) which extends substantially perpendicularly (orthogonal) with the lower support 124, and as shown, substantially perpendicular to the surface 206 and target object (organ) 102 compressed thereupon. It should be noted that although the pre-exposure image may be described as being obtained at an angulation (source position) that is substantially perpendicular to the detector 122, as shown in FIG. 2, the pre-exposure image may be obtained with a source position that may be other than substantially perpendicular to the detector and/or object. For example, in some embodiments, the angulation need not be substantially orthogonal and may be other than orthogonal by up to 13°. That is, whereas FIG. 2 illustrates projection position 204 at a 0° position, e.g. +/−0.5° from perpendicular (along axis 202) to the plane formed by detector 122, the projection position 204 source position for the pre-exposure image, in some embodiments, may be up to 13° from perpendicular to the detector.

The pre-exposure image acquisition comprises a first distinct exposure performed before starting the DBT sweep and is used to determine the attenuation properties of the object 102. In one embodiment, prior to the sweep through a plurality of positions, for example from 210 to 208, the pre-exposure image is obtained at an angulation as close to the central or zero projection 204 position as possible, such as a substantially perpendicular or quasi-perpendicular alignment 202 with the object 102 to be imaged (and substantially perpendicular to the detector 122). Unless otherwise specified, the term substantially used herein means within 5% of the referenced value, and the term substantially as it refers to a particular angle or projection angulation means within five (5) degrees of the referenced value or relationship.

In one embodiment, the x-ray dose in the pre-exposure is not lower than a dose required for an accurate determination of acquisition parameters for the multiple or continuous DBT sweep and may be higher than the dose used for acquiring the DBT central projection. In prior designed systems, once the requisite attenuation properties have been determined and parameters for the DBT sweep established, the pre-exposure image is generally discarded, and a corresponding radiation dose would then be used for subsequently (DBT) imaging the patient. In various embodiments of the methods described herein, the pre-exposure image is not discarded but instead used along with the DBT projections for synthesis of a 2D radiologic image; the pre-exposure image information is therefore used, along with the DBT images, to image the patient, in addition to its use for determining the parameters needed for performing the DBT imaging sequence. An advantage that may be realized by synthesizing a 2D image using both the pre-exposure image and one or more of the tomosynthesis projection images, in the practice of some embodiments of the described systems and methods, is improved image quality obtained within an x-ray dose budget for radiation exposure by the organ (of the patient) being examined, and/or improved image quality without a corresponding increase in an x-ray dose budget, and/or improved image quality while minimizing an x-ray dose budget for obtaining a synthesized 2D image.

The pre-exposure image may be acquired with a different x-ray intensity compared to each projection acquired in order to produce the 3D DBT images. Generally, the intensity level of the pre-exposure image will be higher than for any one of the projections. For the DBT images, there may be, for example, nine different projection views including a zero (or central) projection, which all point to the center of the detector 122. With nine different projection views, for example, including the three views at positions 210, 204, and 208 shown in FIG. 2, each DBT projection may use, for example, ⅑ of the radiation dose budget for the whole DBT sequence. All DBT projection images, therefore, are acquired (each) at a low dose, which is many times lower than the dose needed for a known (standard or conventional) 2D mammogram (or FFDM image). The lower dose results in lower image quality for a particular DBT projection as compared to a standard 2D (FFDM) image. However, continuing with the above example comprising a DBT sequence of nine (9) tomosynthesis projections and using an x-ray dose for the pre-exposure image that is comparable to (or about the same as) the x-ray dose of an individual DBT projection (or ⅑$^{th}$ of the x-ray dose budget for the full DBT sequence), utilizing the pre-exposure image may provide 11% (or ⅑*100%) additional image information for the synthesized 2D image. Carrying this to a DBT sequence comprising N tomosynthesis projections and an x-ray dose used for the pre-exposure image of 1/N of the dose budget for the DBT sequence, utilizing the pre-exposure image may provide 1/N times 100 percent (1/N*100%) additional image data/information usable for improvement of the synthesized 2D image, as compared to existing methods for synthesizing a 2D image using only the tomosynthesis projections.

In performing the DBT sequence, as the emitter 120 is rotated about the organ, the emitter 120 may further include beam shaping (not depicted) to direct the emitted x-rays through the organ 102 to the detector 122. In the embodiment depicted in FIG. 2, the detector 122 is shown integrated into the lower support 124. The emitter 120 is rotatable about the organ 102 to a plurality of orientations with respect to the organ 102. In an exemplary, and non-limiting embodiment, the emitter 120 may rotate through a total arc of 30° relative to the organ 102 or may rotate 30° in each direction (clockwise and counterclockwise) relative to the organ 102. These arcs of rotation are merely exemplary and not intended to be limiting on the scope of the angulation which may be used in embodiments.

Turning now to FIG. 3 is a flow chart of exemplary methods 300 involving pre-exposure image acquisition and determination of parameters of exposure for acquiring DBT images of a target object. Various methods for pre-exposure image acquisition and determination of parameters needed for a subsequent DBT sequence may be used. As shown in FIG. 3 at 310, conventionally, in radiology, the parameters of exposure such as focal track selected (in the case of a device with double focal track), filter used, voltage applied to the tube (kV), presence or absence of grid, enlargement of contact, and product of anodic current by duration of exposure (mA·s), constituting what is called the configuration, are initially determined from a selection of the user for the parameters of presence or absence of grid and enlargement or contact, and from a table of automatic optimization of parameters (AOP) 312, as a function of the selections of the user, for the parameters kV, focal track, filter and mA·s. At 306, the organ part examined is then subjected to a pre-exposure with a low mA·s value to, at 308, determine the characteristics of the organ part examined, in particular the equivalent radiologic thickness, and the parameters of exposure are then adjusted from these characteristics.

At 306, at the time of pre-exposure, an automatic exposure control (AEC) cell may be used and the equivalent radiologic thickness may be determined from the signal of the AEC cell. In order to obtain a reasonable estimate of the equivalent radiologic thickness, numerous different parameters are determined by means of the AEC calibration cell. An estimate of the composition of the organ part examined and an adjustment of the parameters of exposure (configuration) is then made with an initial estimate of mA·s. During an exposure of the organ part examined with the previously determined configuration, the AEC cell continuously updates the mA·s value.

As described in U.S. Pat. No. 6,292,536, a method is provided for adjustment of the configuration, in digital radiology, which does not require the use of a specific calibration cell and requires only a small number of parameters, the method comprising: forming a pre-exposure image and deriving from it a mean pre-exposure detector signal level and converting it into a pre-exposure dose level, determining the equivalent radiologic thickness, estimating a composition of width examined and establishing a configuration of exposure and an exposure mA·s.

Pre-exposure image acquisition is also described in U.S. Pat. No. 6,556,655. According to various embodiments described, the pre-exposure image acquisition and determination of parameters for the DBT projections may include some or all of the method steps comprising: at 302, establishing parameters of pre-exposure from a table of automatic optimization of parameters (AOP's) 312, a given theoretical composition 314 and an estimated radiologic thickness 316 of the organ part examined and for a low but sufficient dose of x-rays to obtain a pre-exposure image of sufficient quality for the differentiation of tissues of the organ part examined; at 304, establishing a minimum dose level and a maximum dose level from a predetermined mechanical thickness of the organ part examined and conversion of these dose levels into a minimum threshold signal level and a maximum signal threshold level, readable by a detector; at 306, pre-exposing the organ part examined to obtain a pre-exposure image; and at 308, establish the parameters of exposure of the organ part examined by x-rays for the DBT sequence.

As mentioned, although the methods described herein are primarily given relative to the examination of a breast, the methods described may be applied to any other organ consisting of other types of tissues and the tissues having various coefficients of attenuation of x-rays. As it relates to mammography, the breast under examination comprises adipose tissue and glandular tissue (mammary gland). In a radiographic examination, the region of the breast to be examined is that made up of glandular tissue, and it is therefore of particular interest to be able to establish the parameters of exposure to x-rays of the breast most adapted to the region of interest comprising the glandular tissue.

After establishment of the parameters of pre-exposure (at 302) from a table of automatic optimization of parameters 312, a given theoretical composition of the breast 314 and an estimated radiologic thickness of the breast 316, and in order for the dose of x-rays to be low but sufficient to obtain a pre-exposure image of sufficient quality for differentiation of the glandular tissue of the breast tissue, (at 304) there are established in a digital imagery x-ray device a minimum dose level and a maximum dose level of x-ray irradiation from a predetermined mechanical thickness of the breast that is converted into a minimum threshold signal level and a maximum threshold signal level, readable by a detector of the device. The parameters of the beam include, among other things, the voltage applied to the x-ray tube (kV), the product of the anodic current multiplied by the duration of exposure (mA·s), the focal track used, the filter, and the positioning (angulation) of the beam.

The given theoretical composition 314 of the breast may be selected as, for example, a theoretical deduction that the breast to be examined comprises approximately 50% fibrous tissue and 50% glandular tissue. Having selected a given theoretical composition 314 of the breast, an estimated radiologic thickness 316 of the breast may be determined corresponding to the mechanical thickness of the breast multiplied by the coefficient of attenuation of x-rays for the theoretical composition of the breast. As an example, with the above selection the estimated radiologic thickness 316 may be 0.93×mechanical thickness; and to maintain a low pre-exposure dose, the mA·s is selected low, for example at a value of 1 to 4.

After pre-exposure of the organ at 306 to obtain a pre-exposure image, establishing the parameters/configuration for the DBT sequence (at 308) may include, for example, creation of a zone of interest of the field of the pre-exposure image and viewing the image in terms of rows and columns of cells, with each cell indexed with regard to a reference point and representing a signal level between a minimum threshold level and a maximum threshold level of a predetermined number of pixels of the detector; and, further, determining absolute minimum signal levels needed for sufficient image quality and differentiation of organ tissue being examined.

Next, FIG. 4 is a flow chart that depicts exemplary embodiments of methods 400 of imaging an organ of a patient using tomosynthesis and synthesizing a 2D image of the imaged organ using pre-exposure image information acquired for determination of parameters (configuration) needed for the tomosynthesis imaging sequence. An exemplary embodiment of a method of imaging an organ of a patient includes obtaining, at 402, a pre-exposure image (for example, at a zero or central projection angulation, or a source position), using a level of x-ray energy, in order to ascertain (at 404) exposure parameters required for, thereafter (at 406), obtaining a plurality of two-dimensional (2D) projection images of the organ by rotating an x-ray emitter (such as emitter 120) to a plurality of orientations relative to the organ and emitting levels of x-ray energization from the emitter for a plurality of projection images. In one embodiment, a pre-exposure x-ray image of the organ is obtained with a first level of x-ray energization, and a levels of x-ray energization are used for the plurality of tomosynthesis projection images that are often less than the level of x-ray energization used for acquisition of the pre-exposure image.

At 408, the central projection image (or projection image closest to the source position projection image) obtained during the DBT sequence (at 406) is enhanced using both data from the DBT projections and data from the pre-exposure image, providing an enhanced central (or source position) projection image. For example, the zero or central projection image (or projection closest to the source position used for the pre-exposure) from the DBT sweep may be used as the baseline or primary view for the synthesized 2D image. Image details present in the pre-exposure image may be extracted and copied into the baseline projection, thereby enhancing the baseline projection. Similarly, image details present in other DBT projections may be extracted and copied into the baseline projection, thereby enhancing the baseline projection. The pre-exposure image may be acquired using a higher x-ray dose (than any of the separate DBT projections) and, therefore, the pre-exposure image may comprise certain details not available in any individual (lower x-ray dose) DBT projection. On the other hand, image details present in various individual DBT projections may be hidden in the pre-exposure image due to superimposition, and such details from the several DBT projection images may be used, along with the pre-exposure image, to enhance the (DBT) baseline projection image. The desired and advantageous result is, therefore, a synthesized 2D image generated by enhancing the baseline projection (from the DBT sweep) using the information from the other views/projections (of the DBT sweep) as well as the pre-exposure image that is used to determine the parameters and configuration for the tomosynthesis imaging sequence. The synthesized 2D image may then be (at 422) displayed (for example, on display 116) for review by the system user or medical practitioner.

In one aspect, the present disclosure is directed to a method for obtaining at least one enhanced image of an object of interest using a system comprising an x-ray source facing a detector. The method comprises, at 402, obtaining a pre-exposure image at a source position or an angulation close to a zero or central projection to, at 404, determine the x-ray parameters for a subsequent DBT sequence; at 406, performing the DBT sequence, comprising acquiring a plurality of 2D (or tomosynthesis) projection images of the object of interest in a plurality of orientations; then, at 410, utilizing the pre-exposure image acquired as a baseline image in place of the zero or central projection (or projection closest to the source position used for the pre-exposure image) acquired during the DBT sequence, effectively replacing the DBT central (or source position) projection with the pre-exposure image; at 416, generating a synthesized 2D image using the projection image acquired from the first distinct exposure (i.e. the pre-exposure) in combination with the projection images acquired during the DBT sequence; and, at 422, displaying the synthesized 2D projection image on a display, such as display 116.

The step 416 of synthesizing a 2D image may comprise using both the pre-exposure image (as a baseline image in place of the central (or source position) projection obtained during the tomosynthesis sequence) and information from at least one of the other tomosynthesis projection images. Similar to methods involving steps 408 and 414, directed to enhancing the tomosynthesis central (or source position) projection using data from both the pre-exposure image and (at least one of) the DBT projection images, information may be extracted and copied from at least one of the tomosynthesis projection images (including, for example, the central (or source position) projection replaced in step 410 with the pre-exposure image) into the pre-exposure image so as to improve content and quality of the resulting synthesized 2D image. The resulting 2D image provides the health professional with a synthesized 2D image for reviewing the object of interest via a display, such as for example display 116.

Another exemplary embodiment of a method of imaging an organ of a patient includes obtaining a pre-exposure x-ray image, using a first level of x-ray energy, in order to ascertain exposure parameters required for, thereafter, obtaining a plurality of two-dimensional (2D) projection images of the organ by rotating an x-ray emitter to a plurality of orientations relative to the organ and emitting a second level (or levels different than the first level) of x-ray energization from the emitter for each projection image of the plurality of projection images. A pre-exposure x-ray image of the organ is obtained with the first level of x-ray energization, with the pre-exposure being the first distinct exposure and the first distinct exposure being acquired along a direction perpendicular or quasi-perpendicular to the image receptor or detector, or along a direction defining a source position at which the pre-exposure image is obtained. The second level of x-ray energization (or levels used in each of the subsequent DBT projections) is often less than the first level of x-ray energization. Then, at 418, the pre-exposure image is merged with at least one of the (DBT sweep) projections closest to the perpendicular to the detector (or closest to the source position used for pre-exposure image acquisition). The merging may be performed using a registration algorithm (at 412) in case of motion and/or to compensate for differences in the acquisition angles. Next, at 420, a synthesized 2D image is generated by enhancing the (merged) pre-exposure image with the information contained in the set of tomosynthesis projection images (from the DBT sequence). The resulting synthesized 2D image may then be, at 422, displayed such as on display 116.

Due to the DBT projection images and the pre-exposure image being acquired during the same compression of the organ and imaging session, which in embodiments uses the same emitter and detector to acquire both the DBT projection images and the pre-exposure image, the pre-exposure image positionally substantially matches the DBT projection acquired at an angulation closest to the zero or central position. In one embodiment, an identifier may be used in a registration algorithm in case of motion (such as patient movement, detector and/or emitter motion, or the like) or (perhaps slight) difference in the angle used for the pre-exposure image versus the angle of the tomosynthesis projection closest to the angle used for the pre-exposure. The identifier may comprise, for example, a maximum intensity voxel found along the ray from the source to each pixel (also known as reprojection operator). These identifiers may be stored in the computer readable memory. These identifiers connect each pixel of the pre-exposure image (and/or subsequently synthesized 2D, and/or an associated 3D volume reconstructed using the DBT projections) to an associated reconstruction slice or DBT projection image from which this pixel stems.

In an optional and exemplary embodiment, the pre-exposure image may be registered to the at least one DBT projection closest to the zero or central projection (or closes to the source position), for registration between the pre-exposure image and the DBT projection image or images with which the pre-exposure image is to be merged. In an embodiment, since the pre-exposure image and the DBT projection images are acquired under a single compression of the breast, the registration process may be simplified due to greater correspondence between the images.

Turning to FIG. 5 is a flow chart of exemplary embodiments of methods 500 of imaging an organ using tomosynthesis, reconstructing a 3D volume using both the set of tomosynthesis projections as well as the pre-exposure image used for determination of parameters for acquiring the tomosynthesis projections. An embodiment of a method of imaging an organ of a patient includes, at 502, obtaining a pre-exposure x-ray image, using a first level of x-ray energy, in order to ascertain exposure parameters required for, thereafter, at 504, obtaining a plurality of two-dimensional (2D) projection images of the organ by rotating an x-ray emitter to a plurality of orientations relative to the organ and emitting a second level (or levels different than the first level) of x-ray energization from the emitter for each projection image of the plurality of projection images. A pre-exposure x-ray image of the organ is obtained with the first level of x-ray energization. The second level of x-ray energization (or levels different than the first level) is often less than the first level of x-ray energization. Then, at 506, a three-dimensional (3D) volume of the organ is reconstructed from the plurality of projection images along with the pre-exposure image. At 508, a synthesized 2D image is then generated out of the reconstructed volume, which may be displayed, at 510, on a display, such as for example display 116.

The pre-exposure image, at 502, may be obtained as described with respect to any of the previous described figures, such as exemplary methods 300, and the DBT projection images, at 504, may be obtained as previously described.

In an exemplary embodiment, the 3D reconstructed volume is reconstructed using a filtered back projection (FBP) reconstruction technique or an iterative reconstruction technique, both of which are known by persons of ordinary skill in the art. The 3D volume may be exemplarily reconstructed using the obtained pre-exposure image as well as at least some of the DBT projection images. In a further exemplary embodiment, a modified filtered projection reconstruction technique may be used wherein greater weight is given to the pre-exposure image in the reconstruction over the contributions of the plurality of DBT projection images.

The 3D reconstruction at 506 may comprise combining the obtained DBT projection images and pre-exposure image prior to the above mentioned reconstruction techniques, and the combination may be accomplished in a variety of ways, or combination methods. In each of these combination methods the pre-exposure image is considered to have been acquired at a position orthogonal to the organ to be imaged, for example at 0° (zero degrees) of rotation, or at a source position that may offset from the orthogonal, while the plurality of DBT projection images are acquired at a plurality of angles relative to the orthogonal, which may include one or more projections at or close to 0° (zero degrees) of rotation (referred to as the zero or central projection in the DBT sequence) or at a projection angulation close to the source position (at which the pre-exposure image was acquired). It will be recognized that while the exemplary embodiments disclosed herein may be described in the context of a pre-exposure image acquired orthogonal to the object, the pre-exposure image may be acquired at another angle while remaining within the scope of the present disclosure; for example, at 410 in the methods 400, the pre-exposure image might be obtained at a source position that is a predetermined offset from zero, and used in place of a DBT projection at or close to the predetermined offset.

In a first combination method, the pre-exposure image is combined with the DBT central projection image for 3D reconstruction; for example, the pre-exposure image and DBT central projection image are combined together (i.e. added together) before reconstruction. In a second combination method, the pre-exposure image is merged with the DBT central (or source position) projection for 3D reconstruction; for example, the pre-exposure may be merged with the DBT projection closest to zero (or closest to the source position) as in method step 418 (i.e. merging the pre-exposure image and DBT projection that is closest to zero or closest to the angulation used for the pre-exposure image) and/or method steps 412 (i.e. using a registration algorithm in case of motion or difference in image angle) and 418, before reconstruction. In a third combination method, the DBT central projection image (or projection closest to the angulation used for the pre-exposure image) is replaced with the pre-exposure image for 3D reconstruction. In a forth combination method, the pre-exposure image compliments the DBT images if, for example, the plurality of DBT projection images does not include a central or orthogonal image. Thus in exemplary embodiments, prior to reconstruction of the 3D volume, the pre-exposure x-ray image is added to the set of 2D (tomosynthesis) projection images, for example in any of the techniques as described above. Then as described in further detail herein, a 3D volume may be created (reconstructed) from the combination of the pre-exposure image and the set of 2D (tomosynthesis) projection images, and, subsequently, a synthesized 2D image may be created from the reconstructed volume.

As previously described, since the organ is under the same compression for both the pre-exposure image and subsequent plurality of DBT projection images, a synthetic 2D image of the 3D reconstructed volume from the position orthogonal to the organ corresponds to the pre-exposure image (acquired orthogonal to the organ). In creating such a synthetic 2D image at 508, various known methods for synthesizing a 2D image from a reconstructed 3D volume may be used. Exemplary methods for image processing and synthesis of a 2D image using tomosynthesis projection images are described in U.S. Pat. No. 9,842,415. The methods may include, for example, as part of reconstructing the 3D volume at 506, applying a filter to the 2D projection images (acquired at 504) so as to obtain filtered projection images of the object of interest. The filtering may include processing the image using a high pass type filter with a cut-off frequency determined based on the thickness of the object of interest (organ) imaged, and/or using a low pass type filter so as to reduce noise. A filtered reconstructed volume of the object of interest may then be generated by reconstructing slices of the object of interest from (at least two of) the filtered projections. The method may then include reprojecting the reconstructed slices according to a determined orientation direction to obtain an intermediate 2D image of the object of interest, and using a pixel-to-pixel linear combination of the intermediate 2D image obtained by the reprojection and at least one of the acquired plurality of 2D projection images or the pre-exposure image corresponding to the determined orientation to obtain a final 2D image of the object of interest. In an exemplary embodiment, the determined orientation direction may be the angulation used for the pre-exposure image and the final 2D image of the object of interest comprises a synthesized 2D image that utilizes both tomosynthesis projection images and a pre-exposure image used to determine parameters for the tomosynthesis projection images.

In the above description, certain terms have been used for brevity, clarity, and understanding. No unnecessary limitations are to be inferred therefrom beyond the requirement of the prior art because such terms are used for descriptive purposes and are intended to be broadly construed. The different systems and method steps described herein may be used alone or in combination with other systems and methods. It is to be expected that various equivalents, alternatives and modifications are possible within the scope of the appended claims.

The functional block diagrams, operational sequences, and flow diagrams provided in the Figures are representative of exemplary architectures, environments, and methodologies for performing novel aspects of the disclosure. While, for purposes of simplicity of explanation, the methodologies included herein may be in the form of a functional diagram, operational sequence, or flow diagram, and may be described as a series of acts, it is to be understood and appreciated that the methodologies are not limited by the order of acts, as some acts may, in accordance therewith, occur in a different order and/or concurrently with other acts from that shown and described herein. For example, those skilled in the art will understand and appreciate that a methodology can alternatively be represented as a series of interrelated states or events, such as in a state diagram. Moreover, not all acts illustrated in a methodology may be required for a novel implementation.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method of generating a synthesized 2D image of an organ of a patient, the method comprising:
   obtaining a pre-exposure image of the organ by exposing the organ with x-ray energization;
   obtaining, based upon the pre-exposure image acquired, a plurality of two-dimensional (2D) tomosynthesis projection images of the organ by rotating the x-ray emitter to a plurality of orientations relative to the organ and emitting x-ray energization from the emitter for each projection image of the plurality of projection images; and
   generating a synthetic 2D image of the organ from the pre-exposure image and the plurality of tomosynthesis projection images.

2. The method of claim 1, wherein the pre-exposure image is merged with at least one of the plurality of 2D projection images prior to generating the synthetic 2D image.

3. The method of claim 2, wherein the merging is performed using a registration algorithm in case of patient motion and/or to compensate for differences in the acquisition angles of the pre-exposure image and the at least one of the tomosynthesis projections.

4. The method of claim 1 further comprising:
   utilizing the pre-exposure image acquired as a baseline image; and
   generating a synthetic 2D image of the organ by enhancing the baseline image with information in the tomosynthesis projection images.

5. The method of claim 2 further comprising:
   utilizing the merged image acquired as a baseline image; and
   generating a synthetic 2D image of the organ by enhancing the baseline image with information in the tomosynthesis projection images.

6. The method of claim 1, further comprising:
   utilizing one of the tomosynthesis projection image as a baseline image; and
   generating a synthetic 2D image of the organ by enhancing the baseline image with information in the tomosynthesis projection images and the pre-exposure image.

7. The method of claim 1, further comprising displaying the synthetic 2D image on a display.

8. The method of claim 1, wherein the pre-exposure image of the organ and the plurality of 2D tomosynthesis projection images of the organ are obtained during a same compression of the organ.

9. The method of claim 1, wherein levels of x-ray energization used for obtaining each of the plurality of two-dimensional (2D) tomosynthesis projection images are lower than a level of x-ray energization used for obtaining the pre-exposure image.

10. A method of generating a synthesized 2D image of an organ of a patient, the method comprising:
    obtaining a pre-exposure image of the organ by exposing the organ with x-ray energization;
    obtaining, based on the pre-exposure image acquired, a plurality of two-dimensional (2D) tomosynthesis projection images of the organ by rotating the x-ray emitter to a plurality of orientations relative to the organ and emitting x-ray energization from the emitter for each projection image of the plurality of projection images;
    reconstructing a 3D volume using the 2D tomosynthesis projection images and the pre-exposure image; and
    generating a synthesized 2D image from the reconstructed 3D volume.

11. The method of claim 10, wherein one of the plurality of 2D tomosynthesis projection images is replaced by the pre-exposure image prior to reconstructing the 3D volume and generating the synthesized 2D image.

12. The method of claim 11, wherein the pre-exposure image is merged with at least one of the plurality of 2D projection images prior to reconstructing the 3D volume and generating the synthetic 2D image.

13. The method of claim 12, wherein the merging is performed using a registration algorithm in case of patient motion and/or to compensate for differences in the acquisition angles of the pre-exposure image and the at least one of the tomosynthesis projections 13.

14. The method of claim 10, wherein the synthetic 2D image is obtained by enhancing the pre-exposure image using at least a subset of the reconstructed slices.

15. The method of 10 further comprising:
    extracting areas of the 3D volume; and
    enhancing the pre-exposure image with the areas extracted from the 3D volume.

16. A system for synthesizing a 2D radiographic image, the system comprising:
    an x-ray emitter capable of producing x-rays, the x-ray emitter being rotatable to a plurality of orientations;
    an x-ray detector in at least partial alignment with the x-ray emitter;

a processor operably connected to the x-ray emitter and the x-ray detector, the processor operates the x-ray emitter and detector to acquire a pre-exposure image of the organ and subsequently, based on the pre-exposure image acquired, operates the x-ray emitter and detector to rotate about an organ to be imaged in order to obtain a plurality of two-dimensional (2D) tomosynthesis projection images of the organ, wherein the processor synthesizes a 2D image from the pre-exposure image and the plurality of tomosynthesis projection images; and a display for displaying the synthesized 2D image.

17. The system of claim 16, wherein the processor merges the pre-exposure image with at least one of the tomosynthesis projection images to create a merged pre-exposure image; and generates the synthesized 2D image of the organ by enhancing the merged pre-exposure image with information in the tomosynthesis projection images.

18. The system of claim 17, wherein the merging is performed using a registration algorithm in case of patient motion and/or to compensate for differences in the acquisition angles of the pre-exposure image and the at least one of the tomosynthesis projections.

19. The system of claim 16, wherein the processor utilizes the pre-exposure image acquired as a baseline image; and generates a synthesized 2D image of the organ by enhancing the baseline image with information in the tomosynthesis projection images.

20. The system of claim 16, wherein the processor enhances a projection image acquired during tomosynthesis exposure using data from the plurality of 2D tomosynthesis projection images; and generates a synthesized 2D image of the organ by using the enhanced projection image.

21. The method of claim 16, wherein levels of x-ray energization used for obtaining each of the plurality of two-dimensional (2D) tomosynthesis projection images are lower than a level of x-ray energization used for obtaining the pre-exposure image.

22. The system of claim 16, wherein the processor reconstructs a 3D volume using the 2D tomosynthesis projection images and the pre-exposure image; and generates a synthesized 2D image from the reconstructed 3D volume.

* * * * *